(12) United States Patent
Chiu et al.

(10) Patent No.: US 9,987,161 B2
(45) Date of Patent: Jun. 5, 2018

(54) URINE PASSING STRUCTURE

(71) Applicants: Chin-Hung Chiu, Taichung (TW);
Chin-Long Chiu, Taichung (TW)

(72) Inventors: Chin-Hung Chiu, Taichung (TW);
Chin-Long Chiu, Taichung (TW)

( * ) Notice: Subject to any disclaimer, the term of this patent is extended or adjusted under 35 U.S.C. 154(b) by 427 days.

(21) Appl. No.: 14/981,865

(22) Filed: Dec. 28, 2015

(65) Prior Publication Data

US 2017/0181886 A1    Jun. 29, 2017

(51) Int. Cl.
*A61F 5/44* (2006.01)
*A61F 5/453* (2006.01)

(52) U.S. Cl.
CPC ............ *A61F 5/453* (2013.01); *A61F 5/4404* (2013.01); *A61F 5/4408* (2013.01)

(58) Field of Classification Search
CPC .......... A61F 5/453; A61F 5/44; A61F 5/4405; A61F 5/451; A61F 5/4556; A61F 5/4453; A61F 5/4408; A61F 5/4404; A47K 11/12
USPC ............................................... 4/144.1–144.4
See application file for complete search history.

(56) References Cited

U.S. PATENT DOCUMENTS

| | | | | | |
|---|---|---|---|---|---|
| 2,534,900 | A | * | 12/1950 | Chalmers | A61F 5/4553 604/330 |
| 3,394,703 | A | * | 7/1968 | Orgel | A61F 5/453 604/353 |
| 3,721,243 | A | * | 3/1973 | Hesterman et al. | A61F 5/4404 604/185 |
| 3,845,766 | A | * | 11/1974 | Zoller | A61F 5/4553 604/330 |
| 4,531,245 | A | * | 7/1985 | Lowd | A47K 11/00 141/337 |
| 4,810,247 | A | * | 3/1989 | Glassman | A61F 5/453 604/171 |
| 4,846,816 | A | * | 7/1989 | Manfredi | A61F 5/4405 604/323 |
| 5,002,541 | A | * | 3/1991 | Conkling | A61F 5/44 604/319 |
| 5,618,277 | A | * | 4/1997 | Goulter | A61F 5/4405 604/349 |
| 8,490,220 | B1 | * | 7/2013 | Hajek | A61F 5/4556 4/144.4 |
| 8,728,048 | B2 | * | 5/2014 | Cisko, Jr. | A61F 5/453 604/349 |
| 2004/0181862 | A1 | * | 9/2004 | Brummer | A61F 5/4556 4/144.4 |

(Continued)

*Primary Examiner* — Matthew F Desanto
(74) *Attorney, Agent, or Firm* — Rosenberg, Klein & Lee

(57) ABSTRACT

A urine passing structure comprises a penis covering portion, a glans protection portion, and a urine guiding portion. The penis covering portion and the urine guiding portion are respectively fluidly communicated with the glans protection portion. A diameter of one end of the glans protection portion fluidly communicated with the penis covering portion is larger than the diameters of the penis covering portion and the urine guiding portion. It is tapered from a top end of the glans protection portion toward a tail end of the urine guiding portion. An accommodating space is defined in the glans protection portion. A passage is passing through the penis covering portion and fluidly communicated with the accommodating space. A urine guiding channel is passing through the urine guiding portion and fluidly communicated with the accommodating space. A one-way urine passing member is arranged in the urine guiding channel.

3 Claims, 6 Drawing Sheets

(56) References Cited

U.S. PATENT DOCUMENTS

| | | | |
|---|---|---|---|
| 2006/0015082 A1* | 1/2006 | Pearson | A61F 5/453 604/347 |
| 2007/0191795 A1* | 8/2007 | Di Croce | A61F 5/4556 604/347 |
| 2008/0015528 A1* | 1/2008 | Chang | A61F 5/453 604/353 |
| 2013/0338617 A1* | 12/2013 | Newton, Jr. | A61F 5/453 604/353 |
| 2014/0310859 A1* | 10/2014 | Brown | A61G 9/006 4/144.1 |
| 2015/0351728 A1* | 12/2015 | Stewart | A61B 10/007 600/573 |
| 2017/0189222 A1* | 7/2017 | Lin | A61F 5/4405 |

\* cited by examiner

URINE PASSING STRUCTURE

BACKGROUND OF THE INVENTION

1. Field of the Invention

The present invention relates to a urine passing structure in medical field and for actual living use, and especially relates to a urine passing structure capable for arranged at an underpants to firmly cover a front end of a male genitalia so as to provide people with disabilities to smoothly pass urine.

2. Description of Related Art

With the advance of science and technology, the present medical facilities have breakthrough changes. In early period, when people with disabilities need to pass urine, parts of them are supported by a medical auxiliary equipment, such as a walking stick or a wheelchair, to step-by-step walk to toilet but another parts of them are unable to walk. Those who are unable to walk must depend on other kinds of medical auxiliary equipment, such as an urinal, a urine collection bag, or a urine collection barrel, to collect the urine. After collecting the urine, the medical auxiliary equipment, such as a urinal, a urine collection bag, or a urine collection barrel, must be cleaned for reuse.

The above mentioned people (or patients) may still have abilities to control themselves. If the people (or patients) are vegetable, epilepsy, Poliomyelitis, and so on who are unable to control themselves to pass urine, the situation of spilling urine may be happened to result in dirtying the environments and further rampant mosquitos and flies. Lots of them are diapered diapers to prevent from spilling urine. However, if the diaper is absorbed too much urine, the skin may contacted with the diaper and have the skin diseases, such as skin ulceration, skin allergy, or skin corruption, to result in the people (patients) having a pain in the neck. Besides, there are some people are inconvenient to go to toilet, such as people who are wearing cleanroom garment and working in clean room. They must take off and put on the cleanroom garment while and after they want to go to toilet to pass urine. It may delay the work time. Therefore, in order to prevent from dirtying the environments, having skin diseases, and delaying work and living time, a medical facility is disclosed and provided relevant people to collect urine and then prevent from spilling urine while passing urine.

Please refer to Taiwanese patent no. M262023, it disclosed a "structure of men's underpants with urine bag". It mainly comprises a pants body and a urine bag body. An opening is formed at a front side of the pants body, and a connection member is surrounded a peripheral of the opening. A receiving bag is arranged at the pants body. The urine bag body is a good tenacity and waterproof bag and may be arranged in the receiving bag of the pants body. Two end of a catheter are respectively fluidly communicated with the urine bag body and a urine guiding cover. A connection member is arranged at an edge of the urine guiding cover. The connection member of the urine guiding cover may be fluidly communicated with the connection member of the pants body. An absorbent cotton with good absorbency may be arranged in the urine bag body. Therefore, the user (patient) may put on the pants body and the male genitalia may be exposed from the opening to be covered in the urine guiding cover so that the urine may be guided from the catheter to the inside of the urine bag body and absorbed by the absorbent cotton.

Even though the situation of spilling urine may be prevented while passing urine, the urine guiding cover is tightly contacted with the skin of the male genitalia for a long time to form a confined space and then to result in the skin diseases due to the moistures generated from the urine. Therefore, how to improve to meet user's (or patient's) demands and uses is necessary.

In view of the foregoing circumstances, the inventor has invested a lot of time to study the relevant knowledge, compare the pros and cons, research and develop related products. After quite many experiments and tests, the "urine passing structure" of this invention is eventually launched to improve the foregoing shortcomings, to meet the public use.

SUMMARY OF THE INVENTION

An object of this invention is providing a urine passing structure. Besides people with disabilities or who are inconvenient to use the toilet may be smoothly passing urine, the situation of spilling urine to influence environments may be prevented and the skin of the male genitalia may be prevented from being contacted to result in having skin diseases. It may improve the drawbacks of the prior art about spilling urine to influence environments and having skin diseases through contacting tightly with the male genitalia.

In order to achieve the above mentioned object, a urine passing structure, covered at a front end of a male genitalia, the urination structure comprises a penis covering portion, a glans protection portion, and a urine guiding portion, wherein: the penis covering portion and the urine guiding portion are respectively fluidly communicated with two ends of the glans protection portion, a diameter of the end of the glans protection portion fluidly communicated with the penis covering portion is larger than a diameter of the penis covering portion and a diameter of the urine guiding portion, an outer peripheral from a top end of the glans protection portion toward a tail end of the urine guiding portion is tapered, an accommodating space is defined in the glans protection portion, a passage is passing through the penis covering portion and fluidly communicated with the accommodating space, and a urine guiding channel is passing through the urine guiding portion and fluidly communicated with the accommodating space; a spiral urine guiding convex block is protruded from a top end of an inner wall surface of the glans protection portion toward a tail end of an inner wall surface of the urine guiding portion, a top surface of the spiral urine guiding convex block is a guiding inclined surface inclined from the inner wall surfaces of the glans protection portion and the urine guiding portion toward centers thereof; and a one-way urine passing member is arranged in the urine guiding channel, a urine passing hole is passing through the one-way urine passing member, two films are extended outwardly from an end of the one-way urine passing member opposite to the male genitalia, and one end of each film is connected with each other so as to form an opening fluidly communicated with the urine passing hole.

In some embodiments, a thickness of the glans protection portion is larger than a thickness of the penis covering portion so as to protect the front end of the male genitalia which is frail.

In some embodiments, a connection of the inner wall surface of the glans protection portion and an inner wall surface of the passage of the penis covering portion is round.

In conclusion, the advantage is providing user(s) for more convenient operation. The urine passing structure of the present invention is indeed capable for preventing from spilling urine and holding back urine. And further, it is adequately ventilated for the male genitalia so as to decrease the rate pf having skin diseases.

The various objectives and advantages of the present invention will be more readily understood from the following detailed description when read in conjunction with the appended drawing.

DETAILED DESCRIPTION OF THE INVENTION

Figure 1:
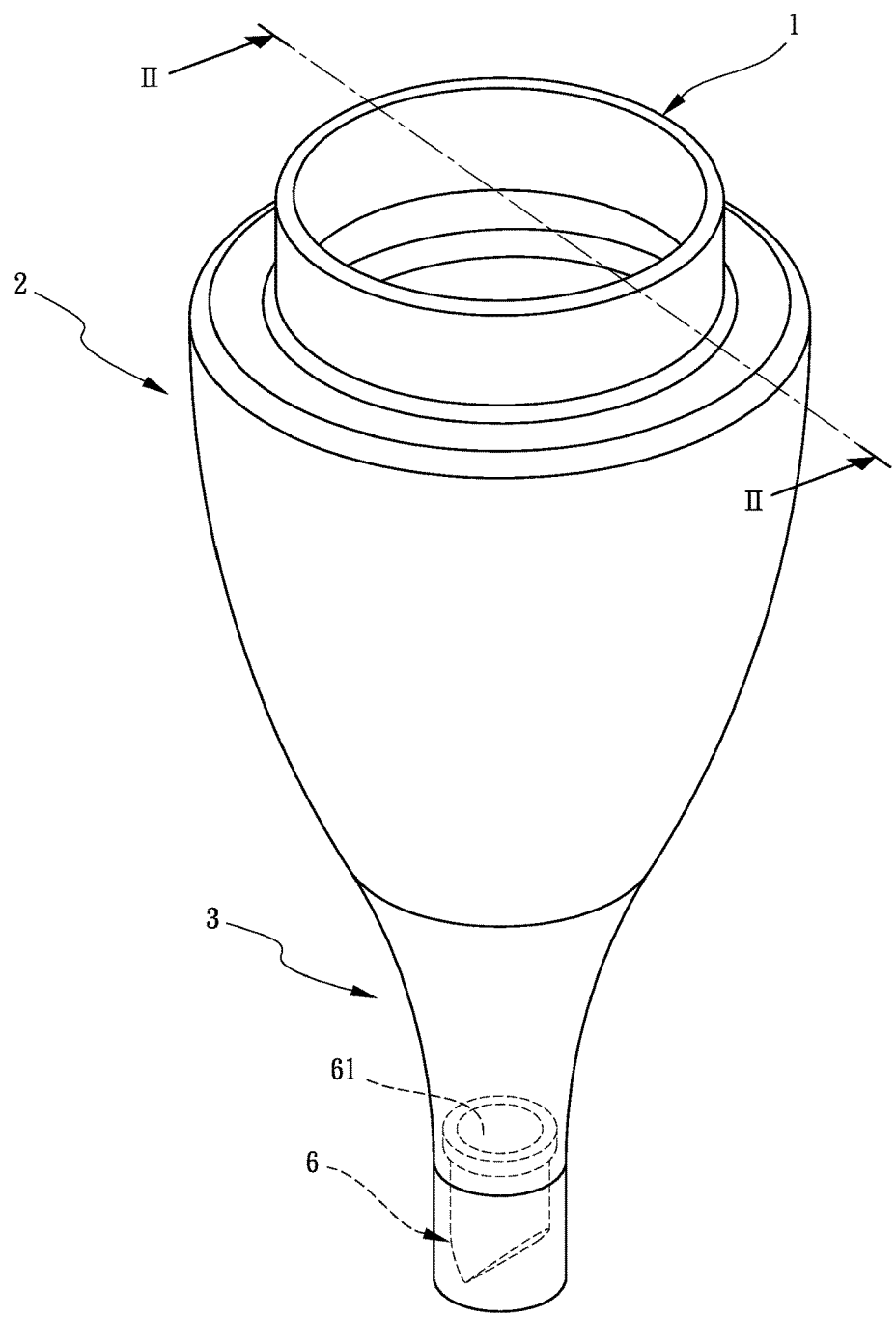
FIG. 1 is a perspective view of a urine passing structure of the present invention.

To describe clearly that the present invention achieves the foregoing objective and function, the technical features and desired function are described with reference to a preferred embodiment and accompanying drawings.

Please refer to FIGS. 1 to 4, a urine passing structure of the present invention may be covered at a front end of a male genitalia. The urine passing structure may comprise a penis covering portion 1, a glans protection portion 2, and a urine guiding portion 3. The penis covering portion 1 and the urine guiding portion 3 are respectively fluidly communicated with two ends of the glans protection portion 2. A diameter of the end of the glans protection portion 2 fluidly communicated with the penis covering portion 1 is larger than a diameter of the penis covering portion 1 and a diameter of the urine guiding portion 3. An outer peripheral from a top end of the glans protection portion 2 toward a tail end of the urine guiding portion 3 is tapered. An accommodating space 4 is defined in the glans protection portion 2. A passage 11 is passing through the penis covering portion 1 and fluidly communicated with the accommodating space 4. A urine guiding channel 31 is passing through the urine guiding portion 3 and fluidly communicated with the accommodating space 4. A spiral urine guiding convex block 5 is protruded from a top end of an inner wall surface of the glans protection portion 2 toward a tail end of an inner wall surface of the urine guiding portion 3. A top surface of the spiral urine guiding convex block is a guiding inclined surface 51 which is inclined from the inner wall surfaces of the glans protection portion 2 and the urine guiding portion 3 toward the centers thereof. A one-way urine passing member 6 is arranged in the urine guiding channel 31. A urine passing hole 61 is passing through the one-way urine passing member 6. Two films 62 are extended outwardly from an end of the one-way urine passing member 6 opposite to the male genitalia. And one end of each film 62 is connected with each other so as to form an opening 63 which is fluidly communicated with the urine passing hole 61.

People with disabilities or who are inconvenient to use the toilet may be covered with the urine passing structure of the present invention. The male genitalia is passing through the passage 11 of the penis covering portion 1 and then the penis covering portion 1 is covered the root of the male genitalia so that the front end of the male genitalia is received in the glans protection portion 2. Therefore, people with disability may not take pants or underpants off but the urine may be passed and guided by the urine guiding portion 3. The outer peripheral of the glans protection portion 3 is tapered from the top end toward the tail end. The outer peripheral of the end of the glans protection portion 2 fluidly communicated with the urine guiding portion 3 is arc and concave. The connection of the inner wall surface of the glans protection portion 2 and the inner wall surface of the urine passing portion 3 are arc and convex. Please refer to FIGS. 1 to 5, urine may be smoothly guided to flow out but not result in the urine being deposited or reflected due to the tapered glans protection portion 2 and the arc and convex connection of the inner wall surface of the glans protection portion 2 and the inner wall surface of the urine guiding portion 3 while people with disabilities are passing urine. In addition, the urine may be passed through the opening 63 due to the design of two films 62 to prevent the urine from backflow after the urine is passed through the urine passing hole 61 with the one-way urine passing member 6. It may prevent the urine from influencing the hygiene of a patient.

For a man, the genitalia is the most important, the most sensitive, and the frailest region. In order to secure the genitalia, the thickness of the glans protection portion 2 is thicker than the thickness of the penis covering portion 1 and the thickness of the urine guiding portion 3. In this embodiment, the thickness of the glans protection portion 2 is equal to the thickness of the urine guiding portion 3 to prevent the front end of the male genitalia from hitting to hurt. When the male genitalia is stayed sultry or stuffy for a long time, the moisture may be generated from the sweat and the urine and further the male genitalia may have skin diseases due to sensitivity of the male genitalia. Therefore, the inner wall surface of the glans protection portion 2 is separated from the outer peripheral of the front end of the male genitalia an adaptive distance so that the front end of the male genitalia may not be contacted with the inner wall surface of the glans protection portion 2 to prevent the male genitalia from having skin diseases. Please reference to FIGS. 3 to 5, the urine guiding channel 31 of the urine guiding portion 3 is fluidly communicated with the accommodating space 4 of the glans protection portion 2 so that the moisture in the glans protection portion 2 may be passed through the urine guiding channel 31 to outside and circulated with the outside air to make the moisture in the glans protection portion 2 not deposit in the accommodating space 4 to result in the skin diseases of the male genitalia.

Figure 2:
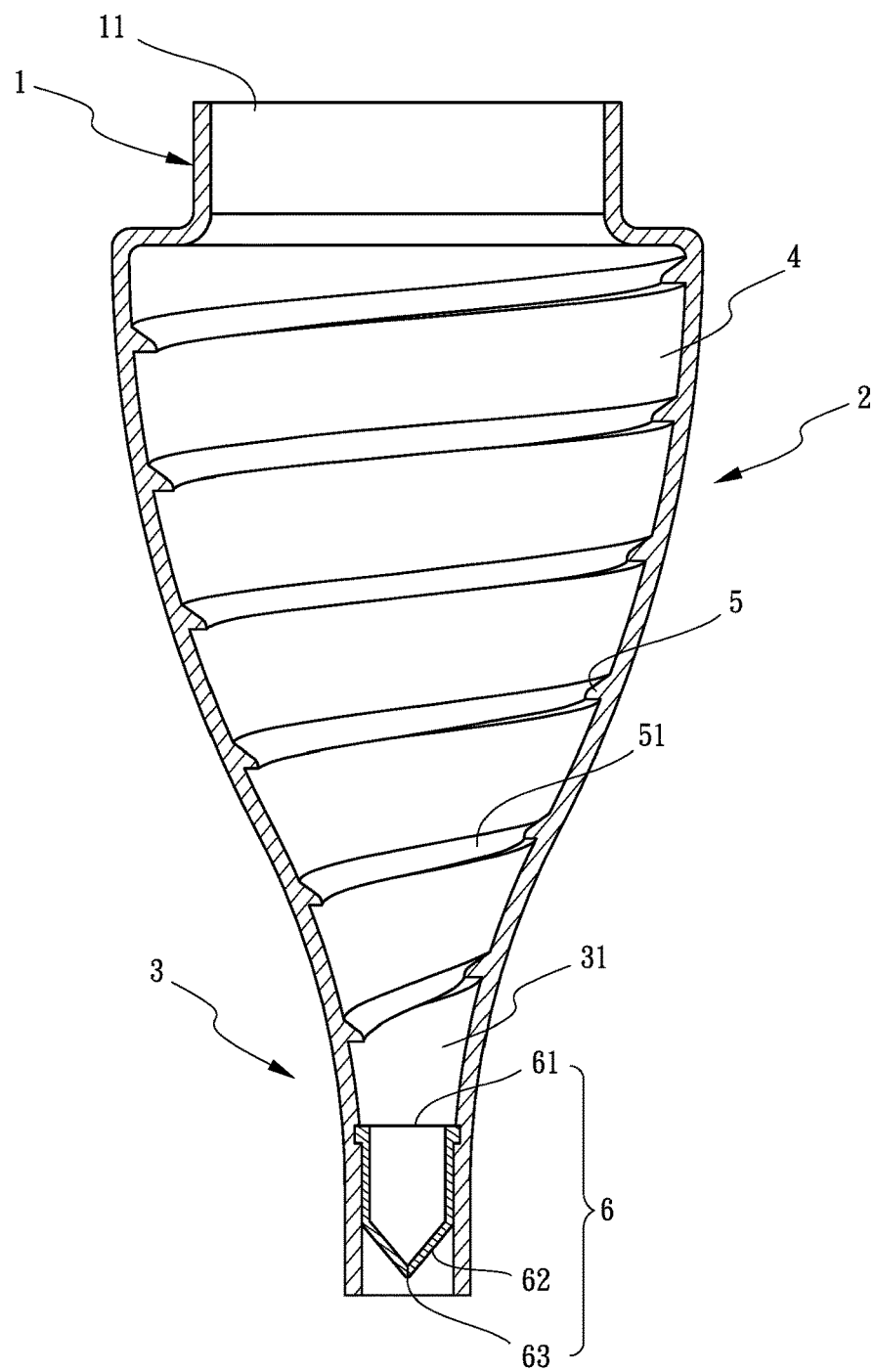
FIG. 2 is a cross-sectional view of FIG. 1 along line II-II.
Figure 3:
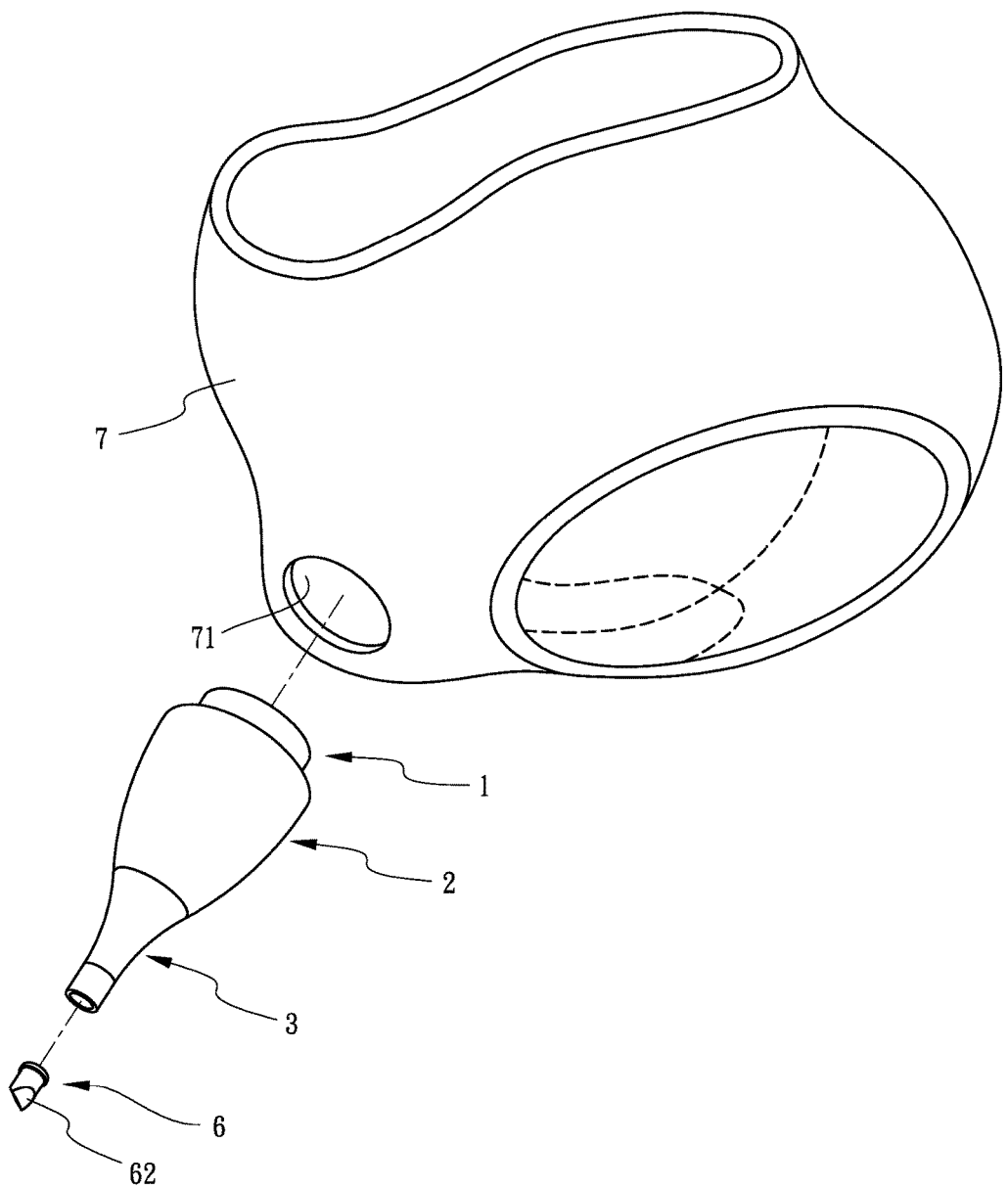
FIG. 3 is an exploded view of the urine passing structure of the present invention and an underpants.

Please refer to FIG. 2, in order to prevent the male genitalia from being scratched to result in bacterial infection, the connection of the inner wall surface of the glans protection portion 2 and the inner wall surface of the penis covering portion 1 is round so as to prevent the front end of the male genitalia from being scratched and slashed to result in inflammation and bacterial infection.

Figure 4:
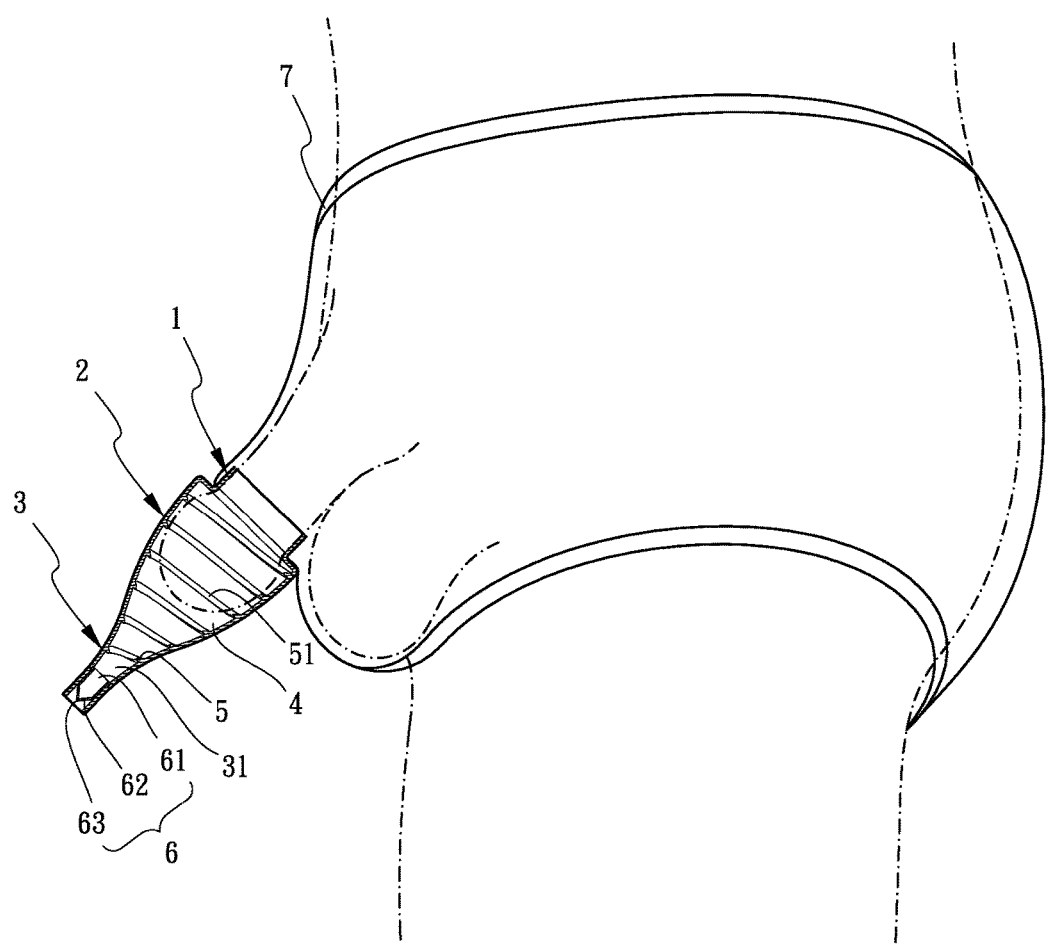
FIG. 4 is a cross-sectional view of the urine passing structure while arranged at the underpants and covered on the male genitalia.
Figure 5:
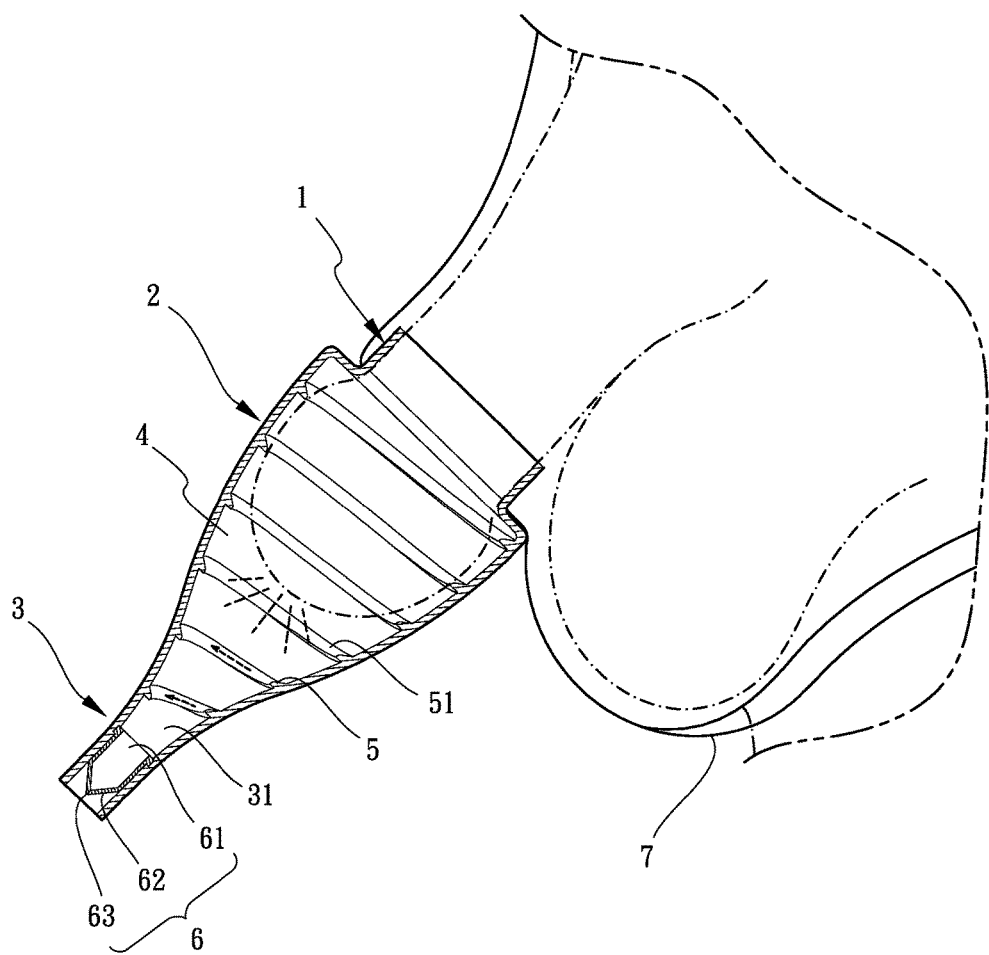
FIG. 5 is a partially enlarged view of FIG. 4.

Please refer to FIGS. 2, 4, and 5, the urine guiding speed may be improved with the urine guiding convex block 5 which is protruded from the top end of the inner wall surface of the glans protection portion 2 toward the tail end of the inner wall surface of the urine guiding portion 3. The urine guiding convex block 5 is spirally arranged at the inner wall surfaces of the glans protection portion 2 and the urine guiding portion 3. When people with disabilities are passing urine, the urine may be guided by the spiral urine guiding convex block 5 and flowed from the glans protection portion 2 toward the urine guiding portion 3 and then guided by the one-way urine passing member 6 to flow outside. The situation of spilling urine may be reduced and improved.

The side of the urine guiding convex block 5 corresponding to the penis covering portion 1 is the guiding inclined surface 51 which is inclined from the inner wall surfaces of the glans protection portion 2 and the urine guiding portion 3 toward the centers thereof. When people with disabilities are passing urine or finish passing urine, the urine may be guided by the guiding incline surface 51 to flow out and prevent the urine from remaining on the inner wall surface of the glans protection portion 2 or the urine guiding portion 3. Besides, the speed of guiding urine may be increased and improved. (Increasing the speed of guiding urine is the main technical characteristics of the present invention, but not limited thereto. The glans protection portion 2 and the urine guiding portion 3 may be also made by smooth materials so as to make the urine not deposit or stay on the inner wall surfaces thereof.)

In order to make sure that the urine is indeed guided by the urine passing hole 61, the connection of the outer peripheral of the one-way urine passing member 6 and the inner wall surface of the urine guiding channel 31 of the urine guiding portion 3 may be in the manners of screwing, engaging, adhering, and integrating. Therefore, the urine may be indeed passed through the urine passing hole 61 so as to prevent the urine from permeating a gap between the one-way urine passing member 6 and the urine guiding channel 31 to result in generating peculiar smell. Please refer to FIG. 2, the connection of the one-way urine passing member 6 and the urine guiding portion 3 is in the manners of engaging.

Figure 6:
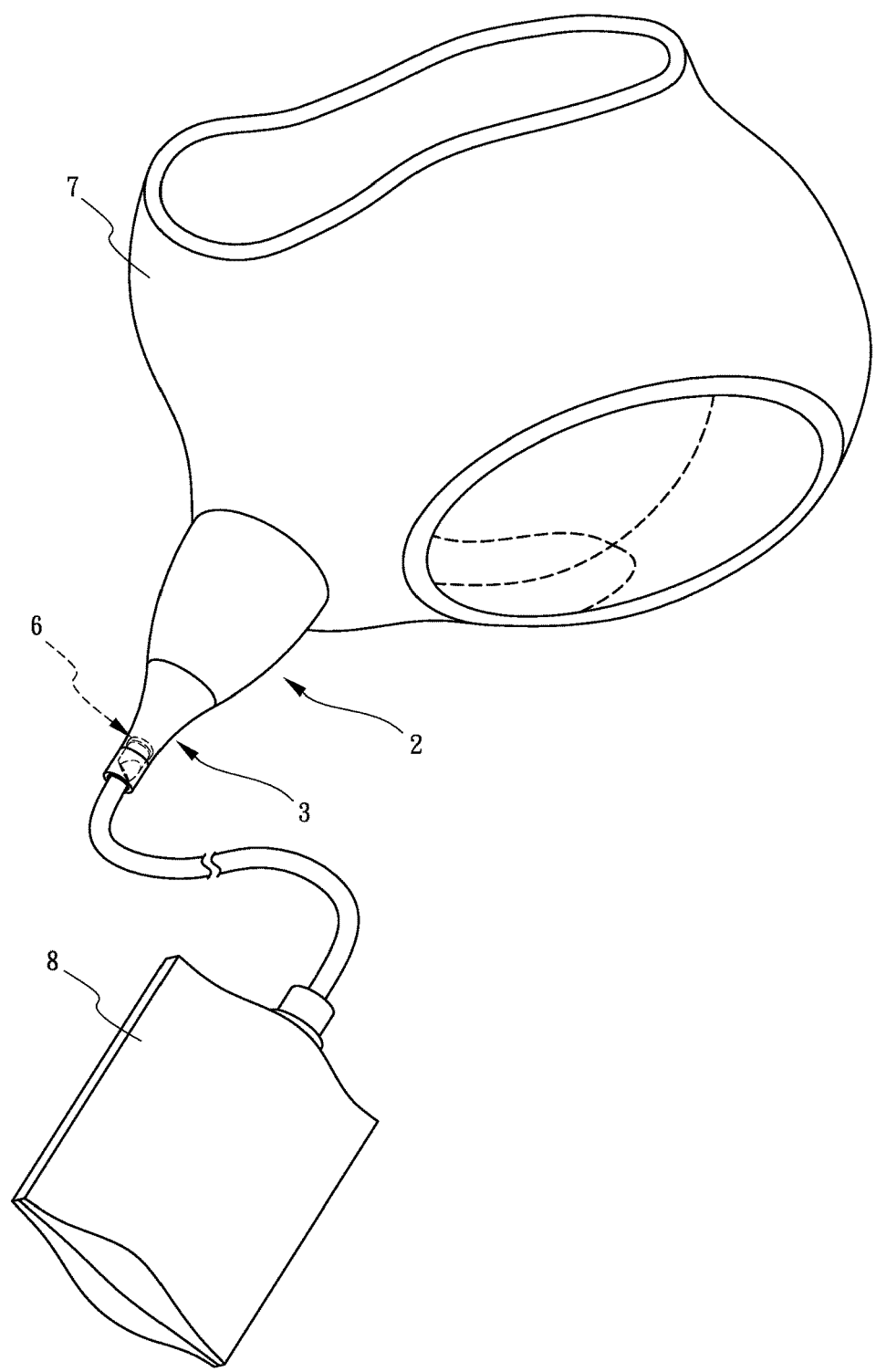
FIG. 6 is a perspective view of a urine guiding portion of the urine passing structure of the present invention whose tail end has arranged a urine collection bag.

According to above descriptions, the urine passing structure of the present invention may be apply to any kinds of underpants. The urine passing structure may be easily arranged at a through hole 71 of the underpants 7 corresponding to the male genitalia. One end of penis covering portion 1 is inserted into the through hole 71 of the underpants 7 and then covered the male genitalia. The glans protection portion 2 and the urine guiding portion 3 are exposed outside the underpants 7. Therefore, while people with disabilities are passing urine, they may pass urine without taking underpants 7 off and further the situation of spilling urine may be decreased and improved to prevent from dirtying environments or prevent the male genitalia from bacterial infection. Besides, in FIGS. 3 and 6, a urine collection bag 8 may be connected with the tail end of the urine guiding portion 3 to collect the urine. Therefore, people with disabilities may reduce the time for searching toilets and further they do not need to hold back urine to result in having pathological changes.

The foregoing descriptions are merely the exemplified embodiments of the present invention, where the scope of the claim of the present invention is not intended to be limited by the embodiments. Any equivalent embodiments or modifications without departing from the spirit and scope of the present invention are therefore intended to be embraced.

The disclosed structure of the invention has not appeared in the prior art and features efficacy better than the prior structure which is construed to be a novel and creative invention, thereby filing the present application herein subject to the patent law.

What is claimed is:

1. A urine passing structure, covered at a front end of a male genitalia, the urination structure comprises a penis covering portion, a glans protection portion, and a urine guiding portion, wherein:
    the penis covering portion and the urine guiding portion are respectively fluidly communicated with two ends of the glans protection portion, a diameter of the end of the glans protection portion fluidly communicated with the penis covering portion is larger than a diameter of the penis covering portion and a diameter of the urine guiding portion, an outer peripheral from a top end of the glans protection portion toward a tail end of the urine guiding portion is tapered, an accommodating space is defined in the glans protection portion, a passage is passing through the penis covering portion and fluidly communicated with the accommodating space, and a urine guiding channel is passing through the urine guiding portion and fluidly communicated with the accommodating space;
    a spiral urine guiding convex block is protruded from a top end of an inner wall surface of the glans protection portion toward a tail end of an inner wall surface of the urine guiding portion, a top surface of the spiral urine guiding convex block is a guiding inclined surface inclined from the inner wall surfaces of the glans protection portion and the urine guiding portion toward centers thereof; and
    a one-way urine passing member is arranged in the urine guiding channel, a urine passing hole is passing through the one-way urine passing member, two films are extended outwardly from an end of the one-way urine passing member opposite to the male genitalia, and one end of each film is connected with each other so as to form an opening fluidly communicated with the urine passing hole.

2. The urine passing structure as claimed in claim 1, wherein a thickness of the glans protection portion is larger than a thickness of the penis covering portion so as to protect the front end of the male genitalia which is frail.

3. The urine passing structure as claimed in claim 1, wherein a connection of the inner wall surface of the glans protection portion and an inner wall surface of the passage of the penis covering portion is round.

* * * * *